United States Patent [19]

Knutson et al.

[11] Patent Number: 5,763,428
[45] Date of Patent: Jun. 9, 1998

[54] METHODS OF TREATING SKIN DISORDERS WITH NOVEL 1A-HYDROXY VITAMIN $D_4$ COMPOUNDS AND DERIVATIVES THEREOF

[75] Inventors: Joyce C. Knutson; Charles W. Bishop. both of Madison, Wis.

[73] Assignee: Bone Care International, Inc., Madison, Wis.

[21] Appl. No.: 484,342

[22] Filed: Jun. 7, 1995

Related U.S. Application Data

[63] Continuation-in-part of Ser. No. 265,438, Jun. 24, 1994, which is a continuation of Ser. No. 886,554, May 20, 1992, abandoned, which is a continuation-in-part of Ser. No. 800,045, Nov. 29, 1991, abandoned, which is a continuation of Ser. No. 586,854, Sep. 21, 1990, abandoned.

[51] Int. Cl.⁶ .................................................. A61K 31/59
[52] U.S. Cl. ................................................ 514/167; 552/653
[58] Field of Search .................................................. 514/167

[56] References Cited

U.S. PATENT DOCUMENTS

| | | |
|---|---|---|
| 2,383,446 | 6/1945 | Calcott et al. |
| 3,697,559 | 10/1972 | DeLuca et al. |
| 3,741,996 | 6/1973 | DeLuca et al. |
| 4,195,027 | 3/1980 | DeLuca et al. |
| 4,202,829 | 5/1980 | DeLuca et al. |
| 4,260,549 | 4/1981 | DeLuca et al. |
| 4,362,710 | 12/1982 | Watanabe . |
| 4,555,364 | 11/1985 | DeLuca et al. |
| 4,661,294 | 4/1987 | Holick et al. |
| 4,689,180 | 8/1987 | DeLuca et al. |
| 4,728,643 | 3/1988 | Holick et al. ............ 514/167 |
| 4,866,048 | 9/1989 | Calverley et al. ........ 514/167 |
| 5,157,135 | 10/1992 | Tsuji et al. |
| 5,185,150 | 2/1993 | DeLuca et al. ........... 424/195.1 |

FOREIGN PATENT DOCUMENTS

| | | |
|---|---|---|
| A-0 390 097 | 10/1990 | European Pat. Off. |
| 0 562 497 A1 | 9/1993 | European Pat. Off. |
| BE-A-877 356 | 10/1979 | France . |
| WO 87/00834 | 2/1987 | WIPO . |
| WO 90/10620 | 9/1990 | WIPO . |

OTHER PUBLICATIONS

F. Sato et al., *Biochim. Biophys. Acta*, vol. 1091 (1991) pp. 188–192.

E. Braunwald et al., *Harrison's Principles of Internal Medicine*: Part Eleven, "Disorders of Bone and Mineral Metabolism," Chapter 335, McGraw–Hill, New York, 1987, pp. 1860–1865.

Grab, W., *Z. Physiol. Chem.*, 243:63–89 (1936).

McDonald, F. G., *J. Biol. Chem.*, 114:IVX (1936).

Windaus, A. and Trautmann, G., *Z. Physiol. Chem.*, 247:185–188 (1937).

DeLuca et al., *Arch. Biochem. Biophys.*, 124:122–128 (1968).

*Merck Index*, S. Budavari (ed.), 11th ed., Merck & Co., Rahway, N.J. (1989) pp. 1579, #9930.

Barton et al., *JCS Perkin I*, 1976, 821–826.

Paaren et al., *J. Org. Chem.*, 1980, 45:3253.

Wientroub, S. et al., "The Dichotomy in the Effects of 1,25 dihydroxy vitamin $D_3$ and 24,25 dihydroxy vitamin $D_3$ on Bone Gamma–Carboxyglutamic Acid–Containing Protein in Serum and Bone in vitamin D–Deficient Rats," *Calcif. Tissue Int.* (1987) 40:166–172.

Sjoden, G. et al., *Proc. Soc. Experimental Biol. Med.*, 178:432–436 (1985).

Strugnell et al., *Biochem. Pharm.* vol. 40:333–341 (1990).

Martin and DeLuca, *Am. J. Physiol.* 216:1352–1359 (1967).

Kocienski, P. J., Lythgoe, B. and Ruston, S., *J.C.S. Perkins I*, 1290–1293 (1979).

Tsuji, M. et al., *Bull. Chem. Soc. Jpn.*, vol. 63, No. 8, 2233–2238 (1990).

Crump, D. R., Williams, D. H. and Pelc, B., *J.C.S. Perkins Trans. I*, 2731–2733 (1973).

Chemical Abstracts, vol. 113, No. 1, 2 Jul. 1990, Columbus, Ohio, US; abstract No. 6683y. Y. Tachibana, 'Preparation of 1beta–hydroxyvitamin $D_2$ and $D_3$.' p. 6688; col. 2; *abstract* & JP–A–02 011 563 (nisshin Flour Milling Co.).

Chemistry Letters, No. 8, Aug. 1985, Tokyo, JP, pp. 1131–1132. H. Nemeto et al., 'A stereoselective synthesis of 1 alpha–hydroxy–vitamin $D_3$'; *the whole document*.

*Primary Examiner*—Kimberly J. Prior
*Attorney, Agent, or Firm*—Teresa J. Welch; Stroud, Stroud, Willink, Thompson & Howard

[57] ABSTRACT

The disclosure is of methods of treating various skin disorders, including skin cancer, with compounds of novel 1α-hydroxy vitamin $D_4$ and novel analogues, thereof, including 1,25 dihydroxy vitamin $D_4$ and 1,24 dihydroxy vitamin $D_4$. Novel 1α-hydroxy vitamin $D_4$ compounds and compounds of novel analogues suitable for use in the treatment of such disorders are also disclosed herein.

21 Claims, 2 Drawing Sheets

METHODS OF TREATING SKIN DISORDERS WITH NOVEL 1A-HYDROXY VITAMIN $D_4$ COMPOUNDS AND DERIVATIVES THEREOF

This application is a continuation-in-part of application Ser. No. 08/265,438, filed Jun. 24, 1994, which is a continuation of application Ser. No. 08/886,554, filed May 20, 1992, now abandoned, which is a continuation-in-part of application Ser. No. 07/800,045, filed Nov. 29, 1991, now abandoned, which is a continuation of application Ser. No. 07/586,854, filed Sep. 21, 1990, now abandoned.

TECHNICAL FIELD

This invention relates to biologically active vitamin $D_4$ compounds. More specifically, this invention relates to novel 1α-hydroxy vitamin $D_4$ and novel intermediates used in its synthesis, novel 1,25 dihydroxy vitamin $D_4$, and novel 1,24 dihydroxy vitamin $D_4$.

This invention also relates to a pharmaceutical composition which includes a pharmaceutically effective amount of the novel 1α-hydroxy vitamin $D_4$ compounds, and to a method of controlling abnormal calcium metabolism by administering a pharmaceutically effective amount of the novel compounds.

BACKGROUND

Vitamin D is known to be important in the regulation of calcium metabolism in animals and man. See, *Harrison's Principals of Internal Medicine*: Part Eleven. "Disorders of Bone and Mineral Metabolism, Chapter 335," E. Braunwald, et al., (eds.), McGraw-Hill, New York, 1987, pp. 1860–1865. The two most commonly known, useful forms of vitamin D are vitamin $D_3$ and vitamin $D_2$. Vitamin $D_3$ is synthesized endogenously in the skin of animals and man, whereas vitamin $D_2$ is the form of vitamin D supplied by plants. Vitamin $D_2$ differs from vitamin $D_3$ in that it contains a double bond between C22 and C23 and further contains a C24-methyl group. In man and rats, vitamin $D_3$ and vitamin $D_2$ have equivalent biopotency.

Vitamin $D_4$, also known as irradiated 22,23-dihydroergosterol or 22,23-dihydro vitamin $D_2$ or 22,23-dihydroergocalciferol, differs from vitamin $D_3$ in that it contains a C24 methyl group. Vitamin $D_4$ was first described in 1936. See, Grab, W., *Z. Physiol. Chem.*, 243: 63 (1936); McDonald, F. G., *J. Biol. Chem.*, 114: IVX (1936). See also, Windaus, A. and Trautmann, G., *Z. Physiol. Chem.*, 247: 185–188 (1937). These references report some disagreement as to the level of biological activity of the vitamin suggesting that in the rat, vitamin $D_4$ is one-third or three-fourths as active as vitamin $D_3$ and in the chick, either one-tenth or one-fifth as active as vitamin $D_3$.

A more definitive study of the biological activity of vitamin $D_4$ was made by DeLuca, et al., in 1968. DeLuca, et al., *Arch. Biochem. Biophys.*, 124: 122–128 (1968). There, the authors confirmed that vitamin $D_4$ was less active than vitamin $D_3$. DeLuca, et al., report that, in their hands, vitamin $D_4$ is two-thirds as active as vitamin $D_3$ or vitamin $D_2$ in the rat, and one-fifth as active as vitamin $D_3$ in the chick.

DeLuca, et al., make reference to the fact that "[t]he synthesis of vitamin $D_4$ has apparently been little used since it was first described by Windhaus and Trautmann," and comment, "[t]his is perhaps due to the fact that vitamin $D_4$ is only of academic interest."

To applicants' knowledge, vitamin $D_4$ has remained "only of academic interest" as applicants are unaware of any further study of vitamin $D_4$ since that reported by DeLuca, et al. In fact, *The Merck Index* states with respect to vitamin $D_4$, "Its biological activity seems doubtful." *Merck Index*, S. Budavari (ed.), 11th ed., Merck & Co., Rahway, N.J., (1989) pp.1579, #9930.

Since DeLuca, et al., discovered the active form of vitamin $D_3$, 1,25-dihydroxy vitamin $D_3$, (U.S. Pat. No. 3,697,559) and its synthetic precursor, 1α-hydroxy vitamin $D_3$, (U.S. Pat. No. 3,741,996), most interest has centered on developing therapeutic uses of these active vitamin $D_3$ metabolites. Unfortunately, while the vitamin $D_3$ metabolites held great promise as therapeutic agents, this promise has never been fully realized because of the extreme toxicity of these agents. For example, toxicity limits the efficacy of vitamin $D_3$, its active forms and analogs, to prevent bone loss or restore lost bone. Many studies indicate that at dosages required for these agents to be effective in bone loss prevention or restoration, hypercalcemia and hypercalciuria are problems. It has been reported that 1α-hydroxy vitamin $D_3$ at a daily dose of 2 µg/day (which has been shown in some studies to be effective in preventing loss of bone) causes toxicity in approximately 67% of patients. What is needed is a biopotent vitamin D metabolite of low toxicity, such that the drug is practical as a therapeutic agent.

SUMMARY OF THE INVENTION

The novel compounds of the invention, 1α-hydroxy vitamin $D_4$, 1,25-dihydroxy vitamin $D_4$ and 1,24-dihydroxy vitamin $D_4$, are bioactive forms of vitamin $D_4$. The present inventors have discovered that these active forms of vitamin $D_4$ display much greater biopotency than would be predicted on the basis of the previously reported bioassays of vitamin $D_4$. The present inventors have also discovered, that the bioactive novel compounds are less toxic than would be predicted on the basis of their biopotency. This combination of high activity with low toxicity makes the compounds of the invention useful as therapeutic agents in the treatment of disorders of calcium metabolism. The novel compounds of the invention are advantageously used as the active compounds of pharmaceutical compositions for diseases induced by abnormal metabolism of calcium.

In order to study the novel compounds of the invention, it was necessary to develop processes for their production. One alpha-hydroxy vitamin $D_4$ was made synthetically and in the course of that synthesis, novel intermediates were also produced. 1,25-dihydroxy vitamin $D_4$ and 1,24-dihydroxy vitamin $D_4$ are isolated as biological products of the metabolism of 1α-hydroxy vitamin $D_4$.

Other advantages and a fuller appreciation of the specific adaptations, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which.

DETAILED DESCRIPTION

The present invention provides synthetic 1α-hydroxy vitamin $D_2$ (1α-OH-$D_4$) compounds as well as tosylated and cyclic derivatives of vitamin $D_4$.

As used herein, the terms "biological activity" or "biologically active" are meant to refer to biochemical properties of compounds such as affecting metabolism, e.g., affecting serum calcium concentration, or binding to an appropriate receptor protein, e.g., binding to vitamin D recepter protein.

In one of its aspects, the invention encompasses the biologically active compounds of the general formula (I):

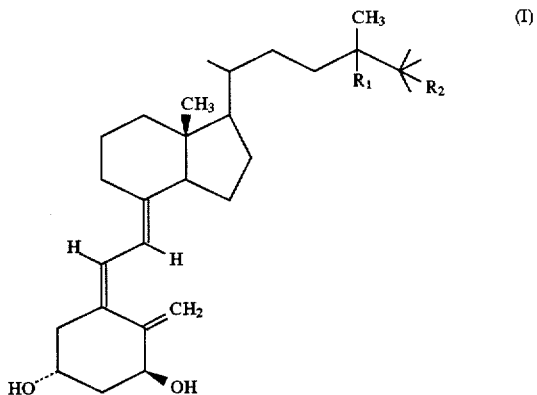

wherein $R_1$ is either H or OH, and $R_2$ is either H or OH, and salts, hydrates and solvates thereof. Preferred compounds among those of formula (I) are those in which $R_1$ and $R_2$ are both H; $R_1$=OH and $R_2$=H; and $R_1$=OH.

Figure 1:
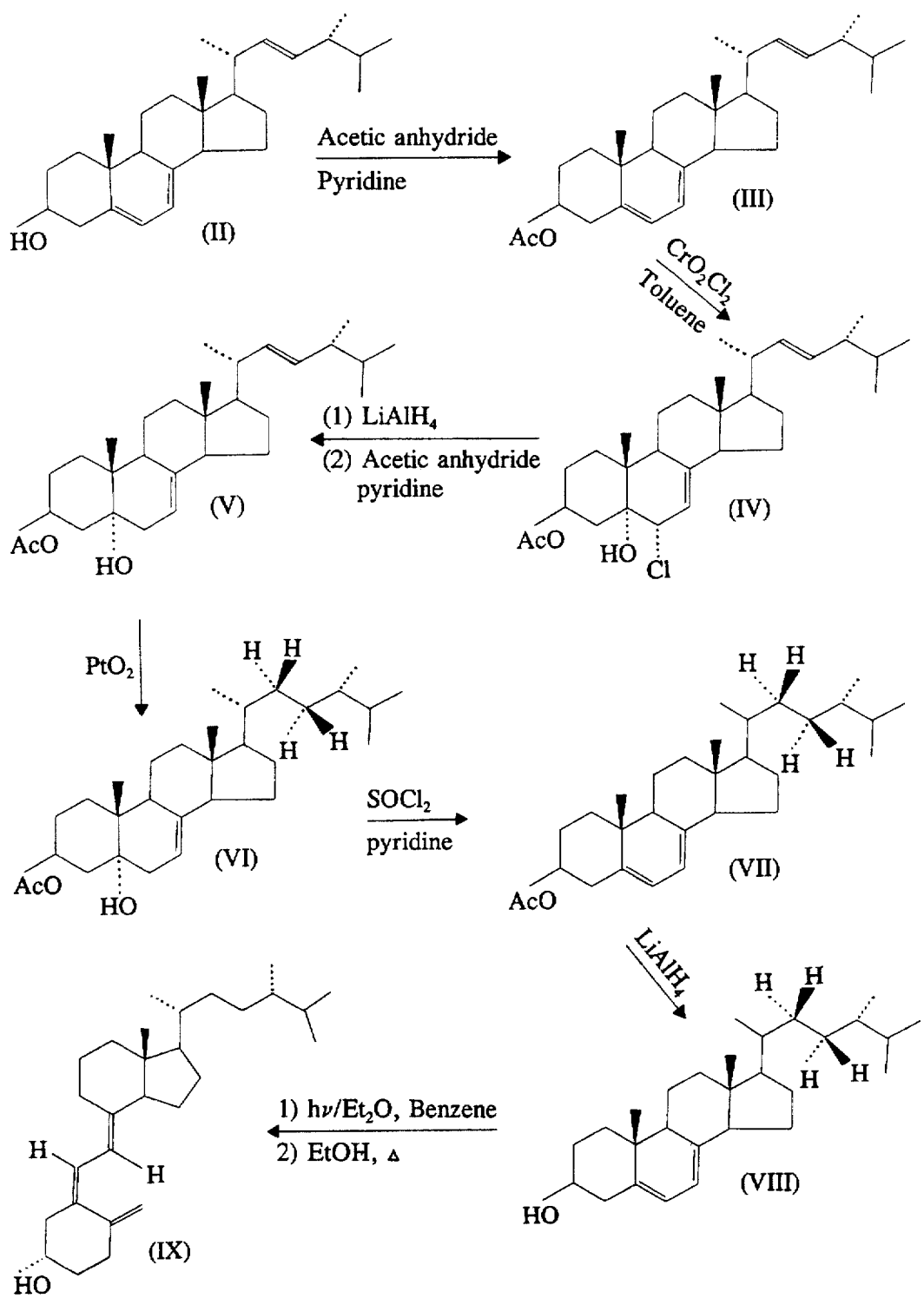
FIG. 1 illustrates preparative steps for the synthesis of vitamin $D_4$.
Figure 2:
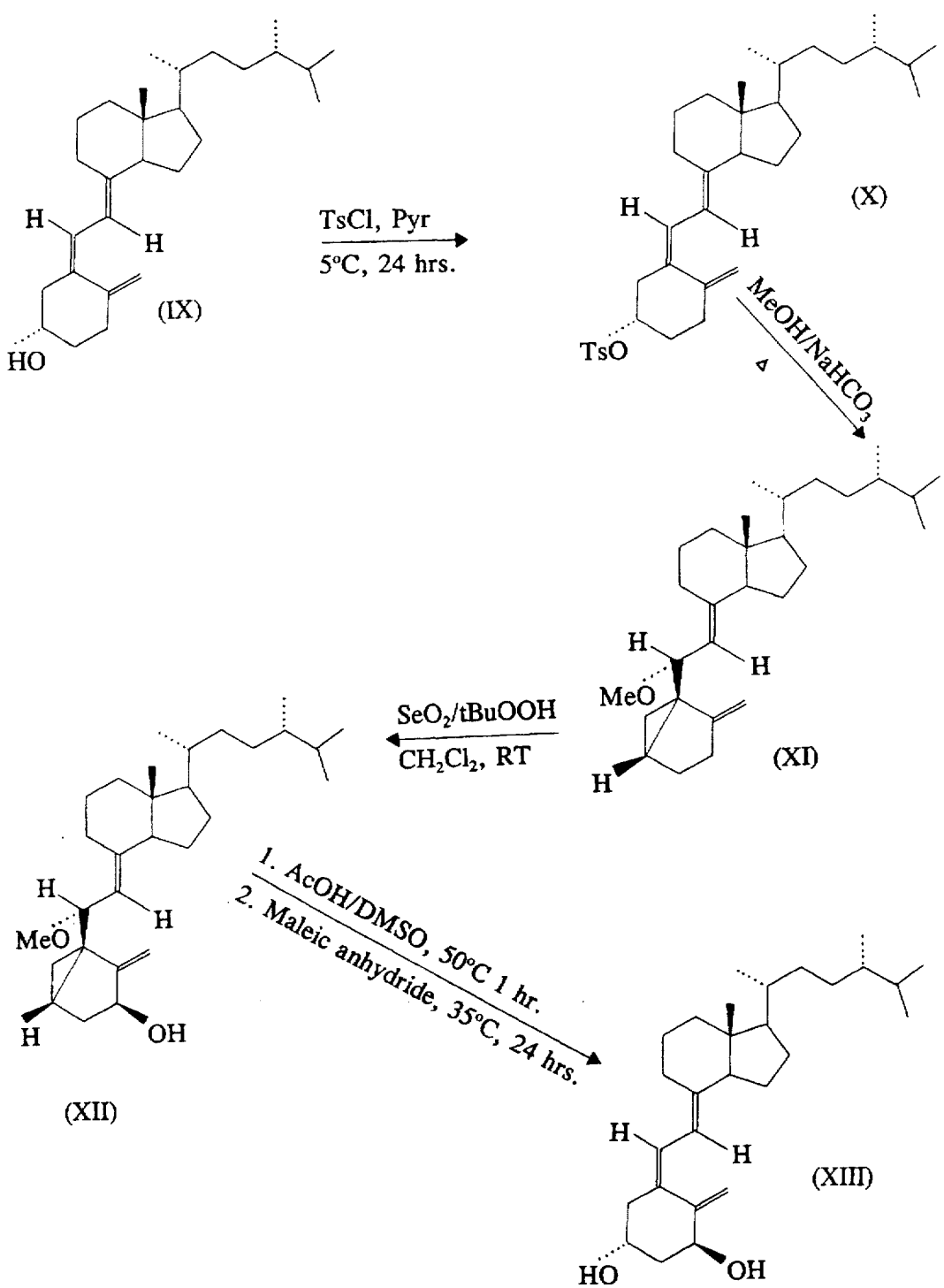
FIG. 2 illustrates preparative steps for the synthesis of 1α-hydroxy vitamin $D_4$ starting with vitamin $D_4$.

In another aspect, the invention involves the preparation of compound of formula (I). Synthesis of 1α-hydroxy vitamin $D_4$, i.e., compounds of formula (I) wherein $R_1$ and $R_2$ are H, is accomplished according to the schema presented in FIGS. 1 and 2. As seen in FIG. 1, the synthesis uses ergosterol as the starting material. Ergosterol undergoes side chain saturation in a six-step process to yield 22,23-dihydroergosterol (VIII) using a procedure similar to that of Barton, et al., *JCS Perkin I*, 1976, 821–826. The 22,23-dihydroergosterol is then irradiated as described in Windaus, et al., *Z. Physiol. Chem.*, 1937, 147: 185, to yield vitamin $D_4$ [22,23-dihydroergocalciferol] (IX). As seen in FIG. 2, vitamin $D_4$ is then hydroxylated in a four-step process to yield 1α-hydroxy vitamin $D_4$ using a procedure similar to that described by Paaren, et al., *J. Org. Chem.*, 1980, 45: 3253.

Specifically, ergosterol is acetylated to form the 3β-acetate. This ergosterol acetate is subjected to hydroxy-halogenation at the 5,6 double bond to form the 6α-chloro-5α-hydroxy derivative. This chlorohydrin is reduced and reacetylated to the 5a-hydroxy (i.e., 5α-ol) derivative. The 5α-ol is subjected to hydrogenation to saturate the side chain. The resulting 3β-acetoxyergost-7en-5α-ol is reduced to 22,23 dehydroergosterol acetate which is in turn reduced to yield 22,23 dehydroergosterol. The 22,23 dehydroergosterol is then irradiated to form vitamin $D_4$. Vitamin $D_4$ is then tosylated to yield 3β-tosyl vitamin $D_4$. The tosylate is displaced by solvolysis to yield the 6-methoxy-3,5-cyclovitamin $D_4$. The cyclovitamin $D_4$ is subjected to allylic oxidation to form the 1α-hydroxy cyclovitamin derivative. The 1α-hydroxy cyclovitamin derivative is sequentially solvolyzed and subjected to a Diels-Alder-type reaction which removes the 5-methoxy group and separates the 1α-hydroxy vitamin $D_4$ (5,6-cis) from the 5,6 trans-1α-hydroxy vitamin $D_4$.

The 1,24 dihydroxy vitamin $D_4$ and 1,25 dihydroxy vitamin $D_4$ metabolites of 1α-hydroxy vitamin $D_4$, are synthesized by incubating the 1α-hydroxy derivatives with human liver cells, culturing the cells, and recovering the 1,24 dihydroxy or 1,25 dihydroxy vitamin $D_4$. Using vitamin D receptor protein binding tests, these metabolites are determined to be biologically active.

The compounds of formula (I) have been found to possess valuable pharmacological activity, namely, as controlling agents for calcium metabolism, especially serum calcium concentrations. Specifically, the compounds of formula (I) increase serum calcium concentrations in rats with vitamin D deficiency. It has also been found that the compounds of formula (I) have low toxicity, which enhances their pharmaceutical properties. Compounds of formula (I) have a toxicity, as measured by the $LD_{50}$ test, which is similar to that of corresponding vitamin $D_2$ compounds and lower than that of corresponding vitamin $D_3$ compounds. Thus, the compounds of the invention are applicable to various clinical and veterinary fields, and are particularly useful for the treatment of abnormal metabolism of calcium and phosphorus.

In a further aspect, the invention entails a method of controlling calcium metabolism, such as for treating abnormal calcium metabolism caused, e.g., by liver failure, renal failure, gastrointestinal failure, etc. The compounds of formula (I) can be used to treat prophylactically or therapeutically vitamin D deficiency diseases and related diseases, for example, renal osteodystrophy, steatorrhea, anticonvulsant osteomalacia, hypophosphatemic vitamin D-resistant rickets, osteoporosis, including postmenopausal osteoporosis, senile osteoporosis, steriod-induced osteoporosis, and other disease states characteristic of loss of bone mass, pseudodeficiency (vitamin D-dependent) rickets, nutritional and malabsorptive rickets, osteomalacia and osteopenias secondary to hypoparathyroidism, post-surgical hypoparathyroidism, idiopathic hypoparathyroidism, pseudohypoparathyhodism, and alcoholism.

The compounds of formula (I), preferably those wherein $R_1$ or $R_2$ is OH, such as 1α,24 dihydroxy vitamin $D_4$, are of value for the treatment of hyperproliferative skin disorders such as psoriasis, eczema, lack of adequate skin firmness, dermal hydration and sebum secretion. Particularly preferred for use in the treatment of such skin disorders is the (R) stereoisomer of 1α,24-dihydroxy vitamin $D_4$, i.e., 1α,24 (R)-dihydroxy vitamin $D_4$, substantially free of its (S) form or in combination with a small quantity of the (S) form. Thus, the present invention provides a method of treating skin disorders by administering to a patient suffering therefrom, a therapeutically effective amount of a compound of formula (I), preferably a compound of formula (I) wherein $R_1$ or $R_2$ is OH, such as 1α,24 dihydroxy vitamin $D_4$. More preferred is the compound of formula (I) which is 1α,24(R)-dihydroxy vitamin $D_4$, substantially free of its (S) form.

The compounds of formula (I), preferably those wherein $R_1$ or $R_2$ is OH, such as 1α,24 dihydroxy vitamin $D_4$, are additionally of value for inhibiting the hyperproliferative activity of malignant cells, i.e., cancer cells. In other words, the compounds of formula (I), particularly, e.g., 1α,24 dihydroxy vitamin $D_4$, act as anti-proliferative agents when exposed to malignant cells. Particularly preferred for use as an anti-proliferative agent is the (R) stereoisomer of 1α,24-dihydroxy vitamin $D_4$, i.e., 1α,24(R)-dihydroxy vitamin $D_4$, substantially free of its (S) form or in combination with a small quantity of the (S) form. Thus, the present invention provides a method of treating malignant cells, e.g., human cancer cells, (i.e., inhibiting their hyperproliferative activity) with an effective amount of a compound of formula (I), preferably a compound of formula (I) wherein $R_1$ or $R_2$ is OH, such as 1α,24 dihydroxy vitamin $D_4$. More preferred is the compound of formula (I) which is 1α,24(R)-dihydroxy vitamin $D_4$, substantially free of its (S) form. The effective amount ranges from about 1 µg/dose to about 500 µg/dose. Of particular value in the treatment of cancers, is the use of the compounds of formula (I) for treatment of skin cancers, which use constitutes another aspect of the invention.

In particular, the compounds of formula (I) are valuable for the treatment of breast cancer and colon cancer. In another aspect, the invention is a method for treating the hyperproliferative cellular effects of breast cancer and colon cancer by admininstering administering to a patient suffering therefrom, a therapeutically effective amount of a compound of formula (I), preferably a compound of formula (I) wherein $R_1$ or $R_2$ is OH, such as $1\alpha,24$ dihydroxy vitamin $D_4$. More preferred is the compound of formula (I) which is $1\alpha,24(R)$-dihydroxy vitamin $D_4$, substantially free of its (S) form.

The compounds of formula (I) are additionally useful in the treatment of noncancerous skin disorders such as dermatitis, contact and ectopic.

The compounds of formula (I) are useful as active compounds in pharmaceutical compositions having reduced side effects and low toxicity as compared with the known analogs of active forms of vitamin $D_3$, when applied, for example, to diseases induced by abnormal metabolism of calcium. These pharmaceutical compositions constitute another aspect of the invention.

The pharmacologically active compounds of this invention can be processed in accordance with conventional methods of pharmacy to produce medicinal agents for administration to patients, e.g., mammals including humans. For example, the compounds of formula (I) can be employed in admixtures with conventional excipients, e.g., pharmaceutically acceptable carrier substances suitable for enteral (e.g., oral), parenteral, or topical application which do not deleteriously react with the active compounds.

Suitable pharmaceutically acceptable carriers include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ or $D_2$ and their $1\alpha$-hydroxylated metabolites, conjugated estrogens or their equivalents, anti-estrogens, calcitonin, biphosphonates, calcium supplements, cobalomin, pertussis toxin and boron.

For parenteral application, particularly suitable are injectable, sterile solutions, preferably oily or aqueous solution, as well as suspensions, emulsions, or implants, including suppositories. Ampoules are convenient unit dosages.

For treatment of cancer, i.e., skin, breast and colon cancers, the parenteral dosage of the compounds of formula (I), preferably $1\alpha,24$-dihydroxy vitamin $D_4$, and more preferably $1\alpha,24(R)$-dihydroxy vitamin $D_4$, substantially free of its (S) form, is about 0.5 µg to about 50 µg/dose.

For treatment of hyperproliferative skin disorders, such as psoriasis, the parenteral dosage of the compounds of formula (I), preferably $1\alpha,24$-dihydroxy vitamin $D_4$, and more preferably $1\alpha,24(R)$-dihydroxy vitamin $D_4$, substantially free of its (S) form, is about 0.5 µg to about 50 µg/dose.

For enteral application, particularly suitable are tablets, dragees, liquids, drops, suppositories, lozenges, powders, or capsules. A syrup, elixir, or the like can be used if a sweetened vehicle is desired.

Sustained or directed release compositions can also be formulated, e.g., liposomes or those in which the active compound is protected with differentially degradable coatings, e.g., by microencapsulation, multiple coatings, etc.

For topical application, suitable nonsprayable viscous, semi-solid or solid forms can be employed which include a carrier compatible with topical application and having a dynamic viscosity preferably greater than water. Suitable formulations include, but are not limited to, solutions, suspensions, emulsions, creams, ointments, powders, liniments, salves, aerosols, transdermal patches, etc., which are, if desired, sterilized or mixed with auxiliary agents, e.g., preservatives, stabilizers, demulsifiers, wetting agents, etc.

Topical preparations of the compound in accordance with the present invention useful for the treatment of skin disorders may also include epithelialization-inducing agents such as retinoids (e.g., vitamin A), chromanols such as vitamin E, β-agonists such as isoproterenol or cyclic adenosine monophosphate (cAMP), anti-inflammatory agents such as corticosteroids (e.g., hydrocortisone or its acetate, or dexamethasone) and keratoplastic agents such as coal tar or anthralin. Effective amounts of such agents are, for example, vitamin A about 0.003 to about 3% by weight of the composition, vitamin E about 0.1 to about 10%; isoproterenol about 0.1 to about 2%; cAMP about 0.1 to about 1%; hydrocortisone about 0.25% to about 5%; coal tar about 0.2 to about 20%; and anthralin about 0.05 to about 2%.

For topical treatment of skin disorders, the dosage of the compounds of formula (I), preferably $1\alpha,24$-dihydroxy vitamin $D_4$, and more preferably $1\alpha,24(R)$-dihydroxy vitamin $D_4$, substantially free of its (S) form, in a locally applied composition is about 1 µg to about 100 µg/gram of composition.

For treatment of cancer, i.e., skin, breast and colon, the dosage of the compounds of formula (I), preferably $1\alpha,24$-dihydroxy vitamin $D_4$, and more preferably $1\alpha,24(R)$-dihydroxy vitamin $D_4$, substantially free of its (S) form, in a locally applied composition is about 1 µg to about 100 µg/gram of composition.

For treatment of hyperproliferative skin disorders, such as psoriasis, the dosage of the compounds of formula (I), preferably $1\alpha,24$-dihydroxy vitamin $D_4$, and more preferably $1\alpha,24(R)$-dihydroxy vitamin $D_4$, substantially free of its (S) form, in a topical composition is about 1 µg to about 100 µg/gram of composition.

For rectal administration, compounds are formed into a pharmaceutical composition containing a suppository base such as cacao oil or other triglycerides. To prolong storage life, the composition advantageously includes an antioxidant such ascorbic acid, butylated hydroxyanisole or hydroquinone.

Oral administration of the pharmaceutical compositions of the present invention is preferred. Generally, the compounds of this invention are dispensed by unit dosage form comprising about 0.5 µg to about 25 µg in a pharmaceutically acceptable carrier per unit dosage. The dosage of the compounds according to this invention generally is about 0.01 to about 0.5 µg/kg/day, preferably about 0.04 to about 0.3 µg/kg/day.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on the age, body weight, general state of health, sex, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

In a still further aspect, the compounds of the present invention can also be advantageously used in veterinary compositions, for example, feed compositions for domestic animals to treat or prevent hypocalcemia. Generally, the compounds of the present invention are dispensed in animal feed such that normal consumption of such feed provides the animal about 0.01 to about 0.5 µg/kg/day.

The following examples are to be construed as merely illustrative, and not limitative of the remainder of the disclosure in any way whatsoever. In the following examples, all temperatures are set forth in degrees Celsius; unless otherwise indicated, all parts and percentages are by weight. Proton nuclear magnetic ($^1$H NMR) spectra were recorded with an IBM Sy-200(200 mHz) and a Bruker Am—400(400 mHz) with aspect 3000 Computer in $CDCl_3$ solutions with $CHCl_3$ as an internal standard. Infrared spectra were recorded with a Fourier transform (FTIR) using samples as potassium bromide (KBr) pellets or as liquids. Mass spectra were recorded with a Finnigan MAT-90 mass spectrometer at 20 eV/Cl. Melting points are determined on a Hoover-Thomas (capillary) Uni-Melt and a Fisher-Johns melting point apparatus (cover-slip type).

EXAMPLE 1

Synthesis of 1α-hydroxy Vitamin $D_4$

Ergosterol (II) was converted to ergosterol acetate (III) by dissolving 100 g (0.25 mol) ergosterol in 600 ml of anhydrous pyridine and 68 ml (0.7 mol) acetic anhydride. The solution was stirred overnight at room temperature after which time the solution was cooled by adding 1.2 L ice, causing a precipitate to form. The precipitate was washed five times with 400 ml portions of water, then once with 400 ml of $CH_3CN$. The resulting product was air dried to yield 79 g (71%) of ergosterol acetate as a white crystalline solid and had the following characteristics: melting point (m.p.): 169°–171° C.; $^1$H NMR: (400 MHz, $CDCl_3$), δppm 2.05 (3H, s, 3β-$CH_3CO$), 4.65–4.75 (1H, m, 3α-H) 5.15–5.25 (2H, m, 22-H and 23-H), 5.4 (1H, d, 6-H), 5.6 (1H, d, 7-H); FTIR [KBr]: 1734 $cm^{-1}$ (C=O stretching) 968 $cm^{-1}$ (C-H bending).

Ergosterol acetate (III) (26 gm, 0.062M) was dissolved in 2.5 L of freshly distilled deoxygenated toluene. To this solution 9 ml (0.111 mol) chromyl chloride dissolved in 240 ml dry $CH_2Cl_2$ was added under nitrogen at −78° C. over a thirty minute period. The reaction system was stirred at −78° C. for an additional fifteen minutes, and then 62 ml of a saturated solution of sodium borohydride in ethanol was added in one portion. After stirring at −78° C. for an additional fifteen minutes, the reaction solution was poured into a two phase system of 3N hydrochloric acid (3 L) and benzene (3 L). The organic layer was separated, then washed with water (2 L), twice with a brine solution (2×1 L) and then dried with anhydrous $MgSO_4$. The dried solution was filtered and concentrated in vacuo. The crude crystalline product was then treated with $CH_3CN$ (280 ml) and filtration of the thus formed slurry yielded 12.5 g (41%) of white crystalline 3β-Acetoxy-6α-chloroergosta-7,22-dien-5α-ol (IV) and had the following characteristics: m.p.: 190°–192° C.; $^1$H NMR: (400 MHz, $CDCl_3$), δppm 2.05 (3H, s, 3β-OAc), 4.65 (1H, d, 6β-H), 5.1 (1H, s, 7-H), 5.1–5.3 (2H, m, 22-H and 23-H); FTIR |KBr]: 1732 $cm^{-1}$ (C=O stretching), 968 $cm^{-1}$ (C-H bending), 3437 $cm^{-1}$ (O-H stretching).

The 3β-Acetoxy 6α-chloroergosta-7,22-dien-5α-ol (IV) (21.4 g, 0.044 mol) in dry THF (900 ml) was added slowly to a stirred suspension of lithium aluminium hydride (2.66 g, 0.07 mol) in dry THF (750 ml) at room temperature under nitrogen. The mixture was refluxed for three hours and cooled to 0° C. Excess hydride was decomposed with saturated $Na_2SO_4$ solution. Filtration through anhydrous $Na_2SO_4$ and evaporation of the filtrate gave a solid, which was treated directly with acetic anhydride (110 ml) and dry pyridine (220 ml) at 0° C. Removal of solvent under reduced pressure yielded the acetate (12.75 g, 61%), 3β-Acetoxyergosta-7,22-dien-5α-ol (V) and had the following characteristics: m.p.: 229°–232° C.; FTIR |KBr] 1736 $cm^{-1}$ (C=O stretching), 3460 $cm^{-1}$ (O-H stretching), 972 $cm^{-1}$ (C-H bending).

3β-Acetoxyergosta-7,22-dien-5α-ol (V) (2.5 g, 0.0055 mol) was shaken for sixteen hours with freshly prepared $PtO_2$ (0.5 g) in ethyl acetate (820 ml) under $H_2$ gas (15 psi). The catalyst was removed by filtration and evaporation of the filtrate gave the crude acetate which was dissolved in $CH_2Cl_2$ and chromatographed on silica gel. Elution with $CH_2Cl_2$ gave substantially pure 3β-Acetoxyergost-7-en-5α-ol (VI) (2.15 g, 85%) as a white crystalline material and had the following characteristics: m.p.: 228°–232° C.; $^1$H NMR: (400 MHz, $CDCl_3$), δppm 2.05 (3H, s, 3β-OAc), 5.05–5.20 (2H, m, 3α-H and 7-H); FTIR [KBr]: 1736 $cm^{-1}$ (C=O stretching), 3462 $cm^{-1}$ (O-H stretching).

Redistilled thionyl chloride (9.7 ml) in dry pyridine (170 ml) was added to compound 3β-Acetoxyergost-7-en-5α-ol (VI) (12.0 g, 0.0262 mol) in dry pyridine (800 ml) at 0° C. under nitrogen. After 2.5 hours, the solution was diluted with ice cold $H_2O$ (1.5 L) and extracted with two portions of ether (2.5 L+1.5 L). The combined ether extracts were washed with a $NaHCO_3$ solution (1.0 L×2), then 1N HCl (1.5 L×2) and then water (1 L). The ether solution was dried with $MgSO_4$, and after filtration, evaporated under reduced pressure to yield a crude product which was converted to a slurry with $CH_3CN$ (100 ml). The product was collected by filtration and recrystallized from $CH_3CN$ to yield 4.5 g. (39%) of a white crystalline 22,23-dihydroergosteryl acetate (VII) and had the following characteristics: m.p.: 144°–147° C.; $^1$H NMR: (400 MHz, $CDCl_3$), δppm 2.05 (3H, s, 3β-OAc), 4.65–4.75 (1H, m, 3α-H), 5.4 (1H, d, 6-H), 5.6 (1H, d, 7-H); FTIR [KBr]: 1734 $cm^{-1}$ (C=O stretching).

22,23-dihydroergosteryl acetate (VII) (4.8 g, 0.011 mol) was added at once to a stirred suspension of lithium aluminium hydride (2.5 g, 0.066 mol) in dry ether (1.1 L) at room temperature. The mixture was stirred for two hours at room temperature. 5N NaOH was added to destroy excess lithium aluminium hydride and $H_2O$ (500 ml) was then added. The aqueous solution was then extracted with four 250 ml portions of ether. The combined ether extracts and combined organic layer were washed with brine solution (1 L), then dried with $Na_2SO_4$. Evaporation of ether under reduced pressure gave the compound, 22,23-dihydroergosterol, (VIII) (4.1 g, 94%) as a white crystalline material and had the following characteristics: m.p.: 147°–150° C.; $^1$H NMR: (400 MHz, $CDCl_3$), δppm 3.6–3.7 (1H, m, 3α-H), 5.4 (1H, d, 6H), 5.6 (1H, d, 7-H); FTIR [KBr]: 3400 $cm^{-1}$ (O-H stretching).

22,23-dihydroergosterol (VII) (2.0 g, 5.0 mmol) was dissolved in a solution of diethyl ether and benzene (4:1, 600 ml) and irradiated (Hannovia immersion lamp, 450 watts) with stirring under argon in a water-cooled quartz vessel for three hours. The solution was concentrated in vacuo to yield a gummy solid, which was redissolved in 100 ml. of ethanol and heated at reflux under argon for eight hours. Then, the solution was concentrated in vacuo and the residue was adsorbed on a silica gel column and eluted with 30% ethyl acetate in hexane to afford vitamin $D_4$ (22,23-dihydroergocalciferol) (IX) with a yield of 1.2 g. (60%) and with the following characteristics: $^1$H NMR: (400 MHz, $CDCl_3$), $\delta$ppm 0.55 (3H, s, 18-$H_3$) 0.78 (6H, dd, 26-$H_3$ and 27-$H_3$) 0.87 (3H, d, 21-$H_3$) 0.93 (3H, d 28-$H_3$) 3.94 (1H, m, 3-H) 4.82 (1H, m (sharp), 19-H), 5.04 (1H, m (sharp), 19-H), 6.04 (1H, d, 7-H) 6.24 (1H, d, 6-H).

To a stirred solution of vitamin $D_4$ (IX) (3.0 g, 7.5 mmol) in 10 ml of dry pyridine was added freshly recrystallized p-toluenesulfonyl chloride (3.6 g, 19 mmol) at 0° C. The reaction mixture was stirred at 5° C. for 24 hours, and was then quenched by pouring the mixture over ice and saturated $NaHCO_3$ (100 ml) with stirring. The aqueous suspension was extracted with $CH_2Cl_2$ (3×300 ml). The combined organic extracts were washed with 10% HCl (3×200 ml), saturated $NaHCO_3$ (3×200 ml) and saturated NaCl (2×200 ml), dried over $MgSO_4$ and concentrated in vacuo to yield 3.5 g. (84%) of the novel intermediate compound vitamin $D_4$ tosylate (X) and had the following characteristics: $^1$H NMR (400 MHz, $CDCl_3$), $\delta$ppm 0.54 (3H, s, 18-$H_3$) 0.78 (6H, dd, 26-$H_3$ and 27-$H_3$) 0.87 (3H, d, 21-$H_3$),0.96 (3H, d, 28-$H_3$) 2.45 (3H, s, $CH_3$ (tosylate) 4.68 (3H, m, 3-H) 4.82 (1H, m (sharp), 19-H) 5.04 (1H, m (sharp), 19-H), 5.95 (1H, d 7-H), 6.09 (1H, d, 6-H) 7.34 and 7.79 (4H, d, aromatic).

To a stirred suspension of $NaHCO_3$ (17.0 g, 202 mmol) in methanol (200 ml) a solution of vitamin $D_4$ tosylate (X) (3.5 g, 6.3 mmol) in dry $CH_2Cl_2$ (10 ml) was added dropwise. The reaction mixture was refluxed overnight under argon, and then cooled to room temperature and concentrated in vacuo to about 50 ml. The reaction concentrate was diluted with ether (600 ml), washed with water (3×300 ml), dried over $MgSO_4$ and concentrated in vacuo. The residue was passed through a silica gel column and eluted with 10% ethyl acetate in hexane to afford the novel intermediate compound 3,5 cyclovitamin $D_4$ (XI) (heavy oil) with a yield of 1.5 g. (58%) and had the following characteristics: $^1$H NMR (400 MHz, $CDCl_3$), $\delta$ppm 0.56 (3H, s, 18-$H_3$) 0.78 (6H, dd, 26-$H_3$ and 27-$H_3$), 0.87 (3H, d, 21-$H_3$), 0.94 (3H, d, 28-$H_3$), 3.28 (3H, s, $OCH_3$) 4.2 (1H, d, 6-H), 4.91 (1H, m (sharp), 19-H), 4.98 (1H, d 7-H), 5.08 (1H, m (sharp), 19-H).

Anhydrous tert-butyl hydroperoxide in toluene (3M) (2.6 ml, 7.8 mmol) was added to a stirred suspension of selenium dioxide (0.22 g, 2 mmol) in dry $CH_2Cl_2$ (150 ml) in a three necked flask. The mixture was stirred for three hours under argon. Pyridine (0.3 ml, 3.7 mmol) was then added, and cyclovitamin $D_4$ (XI) (1.5 g, 3.6 mmol) was then introduced as a solution in $CH_2Cl_2$ (50 ml). After stirring for thirty minutes, 10% aqueous NaOH solution (200 ml) was added. The reaction mixture was then diluted with ether (500 ml) and the phases were separated. The organic phase was washed with 10% NaOH (3×200 ml), water (2×200 ml) and saturated NaCl solution (2×200 ml), dried over $MgSO_4$ and concentrated in vacuo. The residue was absorbed on a silica gel column and eluted with 30% ethyl acetate in hexane to afford 0.45 g. (29%) of the novel intermediate compound 1α-hydroxy 3,5-cyclovitamin $D_4$ (XII) (oil) and had the following characteristics: $^1$H NMR (400 MHz, $CDCl_3$), $\delta$ppm 0.54 (3H, s, 18-$H_3$) 0.78 (6H, dd, 26-$H_3$ and 27-$H_3$) 0.86 (3H, d, 21-$H_3$)0.95 (3H, d, 28-$H_3$) 3.26 (3H, s, $OCH_3$) 4.2 (1H, d, 6-H), 4.22 (1H, m, 1-H), 4.95 (1H, d 7-H), 5.18 (1H, d, 19-H) 5.25 (1H, d, 19-H).

A solution of 1 a-hydroxy 3,5-cyclovitamin $D_4$ (XII) (0.45 g, 1.05 mmol) in a solution of dimethyl sulfoxide (4.5 ml) and glacial acetic acid (3.6 ml) was heated to 50° C. under argon for one hour. The reaction mixture was then poured over ice and saturated $NaHCO_3$ solution (100 ml), and extracted with ether (3×200 ml). The combined ether extracts were washed with saturated $NaHCO_3$ solution (3×200 ml), water (3×200 ml) and saturated NaCl solution (3×200 ml), dried over $MgSO_4$, concentrated in vacuo to give a mixture containing 5,6-cis and 5,6-trans 1α-hydroxy vitamin $D_4$ (about 4:1 by $^1$H NMR) with a yield of 0.4 g. (92%). The mixture of 5,6-cis and 5,6-trans 1α-hydroxy vitamin $D_4$ (0.4 g, 0.97 mmol) was dissolved in ethyl acetate (25 ml) and treated with freshly recrystallized maleic anhydride (0.08 g, 0.8 mmol). This reaction mixture was heated to 35° C. under argon for 24 hours. After evaporation of the solvent in vacuo, the crude mixture was chromatographed over a silica gel column using ethyl acetate and hexane (1:1) as eluent, to afford the novel active form of vitamin $D_4$, 5,6-cis 1α-hydroxy vitamin $D_4$ (XII) with a yield of 90 mg (23%) and had the following characteristics: m.p.: 128°–130° C.; IR $v_{max}$ (Neat): 3400 cm$^{-1}$ (OH stretching); $^1$H NMR (400 MHz, $CDCl_3$), $\delta$ppm 0.55 (3H, s, 18-H) 0.79 (6H, dd, 26-$H_3$ and 27-$H_3$) 0.87 (3H, d, 21-$H_3$) 0.94 (3H, d, 28-$H_3$), 4.24 (1H, m, 3-H), 4.44 (1H, m, 1-H), 5.02 (1 H, m (sharp), 19-H), 5.34 (1H, m (sharp), 19-H), 6.02 (1H, d 7-H), 6.4 (1H, d, 6-H); Mass spectrum [Cl] m/e (relative intensity): 415 (M+1, 41%) 397, (M+1-OH 100%), 379 (27%), 135 (22%).

EXAMPLE 2

Biological Testing of 1α-hydroxy Vitamin $D_4$

Male weanling rats (Holtzman strain, Holtzman Company, Madison, Wis.) were fed a vitamin D deficient diet containing adequate calcium (0.47%) and phosphorus (0.3%). Within three to four weeks, this diet induces an extreme vitamin D deficiency characterized by low serum calcium and poor growth. After four weeks on this diet, the rats had serum calcium values less than 7 mg/dl. The rats were then separated into four groups and orally administered either 1α-hydroxy vitamin $D_4$ in a vehicle such as coconut oil or the vehicle (control) for each of 14 days. Twenty-four hours after the last dose, the rats were killed and the blood calcium measured by a standard laboratory technique. The results of these determinations are shown in Table 1.

TABLE 1

Increase in Serum Calcium Concentration

| Compound | Dose (μg/kg/day) | Number of Rats | Serum calcium concentration (mg/dl) ± Standard Deviation |
|---|---|---|---|
| Control | — | 10 | 6.1 ± 0.48 |
| 1α-OH-$D_4$ | 0.042 | 8 | 7.1 ± 0.80 |
| 1α-OH-$D_4$ | 0.250 | 7 | 11.6 ± 0.45 |
| 1α-OH-$D_4$ | 1.500 | 9 | 12.7 ± 0.37 |

The data of Table 1 indicate that 1α-hydroxy vitamin $D_4$ is effective at increasing serum calcium in the vitamin D deficient rat and that the response appears to be dose dependent. Surprisingly, the level of the response appears to compare favorably to that reported by Wientroub, et. al., for 1,25 dihydroxy vitamin $D_3$ administered to vitamin D deficient rats under experimental conditions similar to those described above. See, Wientroub, S., Price, P. A., Reddi, A. H., "The Dichotomy in the Effects of 1,25 dihydroxy vitamin $D_3$ and 24,25 dihydroxy vitamin $D_3$ on Bone Gamma-Carboxyglutamic Acid-Containing Protein in Serum and Bone in vitamin D-Deficient Rats." *Calcif. Tissue Int.* (1987) 40: 166–172.

EXAMPLE 3

Toxicity Tests

The acute oral toxicity of $1\alpha$-OH-$D_4$ in rats was assessed by determining the mean lethal dose ($LD_{50}$) using a well-known method. Rats were fed a standard laboratory diet for 8–10 weeks. Five animals of each sex were administered one oral dose of $1\alpha$-OH-$D_4$. The animals were observed for 14 days, and the number of deaths noted. The $LD_{50}$ value was determined to be about 1.0 mg/kg in males and 3.0 mg/kg in females.

For comparison, the $LD_{50}$ value for $1\alpha$-hydroxy vitamin $D_2$ under the same conditions was found by applicant's to be 1.7 and 1.8 mg/kg, in male and female rats, respectively. The toxicity of $1\alpha$-hydroxy vitamin $D_2$ has previously been reported as less than $1\alpha$-hydroxy vitamin $D_3$. Sjoden, G., Smith, C., Lindgren, U., and DeLuca, H. F., *Proc. Soc. Experimental Biol. Med.*, 178: 432–436 (1985).

EXAMPLE 4

Generation and Isolation of 1,25-dihydroxy Vitamin $D_4$

The $1\alpha$-hydroxy vitamin $D_4$ of the present invention is incubated with cultured human liver cells which metabolize the compound to several products including the metabolite 1,25 dihydroxy vitamin $D_4$. The 1,25 metabolite is isolated and purified by high pressure liquid chromatography and identified by gas-chromatography-mass spectrometry. Binding studies demonstrate that the 1,25 dihydroxy vitamin $D_4$ has good binding affinity for the mammalian vitamin D receptor protein indicating it is biologically active. The procedures used are similar to that described by Strugnell, et. al., *Biochem. Pharm.* Vol. 40: 333–341 (1990).

EXAMPLE 5

Generation and Isolation of 1,24-dihydroxy Vitamin $D_4$

Generation and isolation of 1,24 dihydroxy vitamin $D_4$ is accomplished as described in Example 4, above. The $1\alpha$-hydroxy vitamin $D_4$ of the present invention is incubated with cultured human liver cells which metabolize the compound to several products including the metabolite 1,24 dihydroxy vitamin $D_4$. The 1,24 metabolite is isolated and purified using high pressure liquid chromatography and identified by gas-chromatography-mass spectrometry. Binding studies with the new metabolite demonstrate that the metabolite has good binding affinity for the mammalian vitamin D receptor protein which indicates the drug is biologically active.

EXAMPLE 6

Hypercalcemia Testing

Female rats are fed a commercial diet containing 0.8% calcium (0.8%) and phosphorus (0.6%). The rats are divided into four groups and each group is orally administered daily either $1\alpha$-OH $D_4$ in a vehicle such as coconut oil or the vehicle (control) alone for 13 weeks. Twenty-four hours after the last dose, the rats are killed and their serum calcium determined by a standard method.

This procedure demonstrates that the serum calcium concentration is unaffected or only slightly elevated at doses $1\alpha$-OH-$D_4$ up to 2.5 µg/kg/day.

EXAMPLE 7

Further Biological Testing

Male weanling rats are fed a diet deficient in vitamin D and with low calcium (0.02%). After a period of four weeks has elapsed, the rats are divided into four groups and intravenously administered either $1\alpha$-OH $D_4$ in a vehicle such as ethanol or the vehicle (control) alone. Sixteen hours after administration, the rats are killed and the intestinal calcium transport measured by using everted duodenal sacs, following the method of Martin and DeLuca, *Am. J. Physiol.* 216: 1352–1359.

Following this procedure demonstrates stimulation of intestinal calcium transport in a dose dependent manner.

EXAMPLE 8

A clinical study is conducted with postmenopausal osteoporotic outpatients having ages between 55 and 75 years. The study involves up to 120 patients randomly divided into three treatment groups, and continues for 12 to 24 months. Two of the treatment groups receive constant dosages of 1a-vitamin $D_4$ (u.i.d.; two different dose levels above 3.0 µg/day) and the other group receives a matching placebo. All patients maintain a normal intake of dietary calcium (500 to 800 mg/day) and refrain from using calcium supplements. Efficacy is evaluated by pre- and post-treatment comparisons of the patient groups with regard to (a) total body, radial, femoral and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with $1\alpha$-vitamin $D_4$ exhibit significantly higher total body, radial, femoral and/or spinal bone densities relative to patients treated with placebo. The treated patients also exhibit significant elevations in serum osteocalcin. Bone biopsies from the treated patients show that $1\alpha$-vitamin $D_4$ stimulates normal bone formation. The monitored safety parameters confirm an insignificant incidence of hypercalcemia or hypercalciuria, or any other metabolic disturbance with $1\alpha$-vitamin $D_4$ therapy.

EXAMPLE 9

A clinical study is conducted with healthy postmenopausal women having ages between 55 and 60 years. The study involves up to 80 patients randomly divided into two treatment groups, and continues for 12 to 24 months. One treatment group receives a constant dosage of $1\alpha$-vitamin $D_4$ (u.i.d.; a dose level above 3.0 µg/day) and the other receives a matching placebo. The study is conducted as indicated in Example 2 above.

This study demonstrates that patients treated with $1\alpha$-vitamin $D_4$ exhibit reduced losses in total body, radial, femoral and/or spinal bone densities relative to baseline values. In contrast, patients treated with placebo show significant losses in these parameters relative to baseline values. The monitored safety parameters confirm the safety of long-term $1\alpha$-vitamin $D_4$ administration at this dose level.

EXAMPLE 10

A twelve-month double-blind placebo-controlled clinical trial is conducted with thirty men and/or women with renal disease who are undergoing chronic hemodialysis. All patients enter an eight-week control period during which time they receive a maintenance dose of vitamin $D_3$ (400 IU/day). After this control period, the patients are randomized into two treatment groups: one group receives a constant dosage of 1α-vitamin $D_4$ (u.i.d.; a dosage greater than 3.0 µg/day) and the other group receives a matching placebo. Both treatment groups receive a maintenance dosage of vitamin $D_3$, maintain a normal intake of dietary calcium, and regrain from using calcium supplements. Efficacy is evaluated by pre- and post-treatment comparisons of the two patient groups with regard to (a) direct measurements of intestinal calcium absorption, (b) total body, radial, femoral and/or spinal bone mineral density, and (c) determinations of serum calcium and osteocalcin. Safety is evaluated by regular monitoring of serum calcium.

Analysis of the clinical data shows that 1α-vitamin $D_4$ significantly increases serum osteocalcin levels and intestinal calcium absorption, as determined by measurements using a single or double-isotope technique. Patients treated with this compound show normalized serum calcium levels, stable values for total body, radial, femoral and/or spinal bone densities relative to baseline values. In contract, patients treated with placebo show frequent hypocalcemia, significant reductions in total body, radial, femoral and/or spinal bone density. An insignificant incidence of hypercalcemia is observed in the treated group.

EXAMPLE 11

Medicament Preparations

A topical cream is prepared by dissolving 1.0 mg of 1α,24-dihydroxy vitamin $D_4$ in 1 g of almond oil. To this solution is added 40 gm of mineral oil and 20 gm of self-emulsifying beeswax. The mixture is heated to liquify. After the addition of 40 ml hot water, the mixture is mixed well. The resulting cream contains approximately 10 µg of 1α,24-dihydroxy vitamin $D_4$ per gram of cream.

EXAMPLE 12

An ointment is prepared by dissolving 1.0 mg of 1α,24-dihydroxy vitamin $D_4$ in 30 g of almond oil. To this solution is added 70 gm of white soft paraffin which had been warmed just enough to be liquified. The ointment is mixed well and allowed to cool. This ointment contains approximately 10 µg 1α,24-dihydroxy vitamin $D_4$ per gram of ointment.

EXAMPLE 13

To the ointment of Example 12 is added with thorough mixing 0.5 g of adenosine and 2.0 g of papaverine base, both dissolved in a minimum quantity of dimethyl sulfoxide. The additional ingredients are present to the extent of about 0.5 wt % (adenosine) and 2 wt % (papaverine base).

EXAMPLE 14

To the ointment of Example 12 is added with thorough mixing 10,000 U of Vitamin A dissolved in a minimum quantity of vegetable oil. The resultant ointment contains about 100 U Vitamin A per gram of the ointment.

EXAMPLE 15

A dermatological lotion is prepared by dissolving 1.0 mg of 1α,24-dihydroxy vitamin $D_4$ in 100 g of dry propylene glycol. The lotion is stored in a refrigerator in a brown bottle and contains about 10 µg of 1α,24-dihydroxy vitamin $D_4$ per gram of lotion.

EXAMPLE 16

In 1 g of almond oil is dissolved 0.2 mg of 1α,24-dihydroxy vitamin $D_4$. To the solution is added 40 g of mineral oil and 20 g of self-emulsifying beeswax, followed by 40 ml of hot water. The mixture is mixed well to produce a cosmetic cream containing about 2.0 µg of 1α,24-dihydroxy vitamin $D_4$ per gram of cream.

EXAMPLE 17

To a cosmetic cream prepared according to example 18 is added 100 mg adenosine. The cream is mixed well and contains about 0.1 wt % adenosine.

EXAMPLE 18

An ointment is prepared by dissolving 100 µg of 1α,24-dihydroxy vitamin $D_4$ in 30 g of almond oil. To the solution so produced is added 70 g white soft paraffin which had been warmed just enough to be liquified. The ointment is mixed well and allowed to cool. The ointment so produced contains about 1.0 µg of 1α,24-dihydroxy vitamin $D_4$ per gram of ointment.

EXAMPLE 19

To the cosmetic ointment of Example 18 is added with thorough mixing 200 U/g Vitamin A dissolved in a minimum amount of vegetable oil.

EXAMPLE 20

A cosmetic lotion is prepared by dissolving 300 µg of 1α,24-dihydroxy vitamin $D_4$ in 100 g of dry propylene glycol. The lotion is stored in a refrigerator in a brown bottle and contains about 3.0 µg 1α,24-dihydroxy vitamin $D_4$ per gram of lotion.

EXAMPLE 21

Dermatological Testing

Compositions containing 1α,24-dihydroxy vitamin $D_4$ are evaluated for therapeutic efficacy of the composition in the topical treatment of dermatitis (contact and ectopic). The composition evaluated is an ointment containing 10 µg of 1α,24-dihydroxy vitamin $D_4$ per gram of ointment in a petrolatum-almond oil base. The control composition is identical except that it does not contain the active agent 1α,24-dihydroxy vitamin $D_4$. The patients are treated in an out-patient clinic. They are instructed to use the preparation two times a day.

The ointment is as far as possible applied to a single lesion, or to an area of the disease. The ointment and its container are weighed before the treatment starts and returned with any unused contents for reweighing at the end of the treatment.

The area of the lesion treated is estimated and recorded, and the lesion is photographed as required, together with suitable "control" lesions. The latter are preferably lesions of similar size and stage of development, either in the vicinity of the treated lesion or symmetrically contralateral. Relevant details of the photographic procedure are recorded so as to be reproduced when the lesions are next photographed (distance, aperture, angle, background, etc.). The ointment is applied twice daily and preferably left uncovered. The "control" lesions are left untreated, but if this is not possible, the treatment used on them is noted.

Evaluations of erythema, scaling, and thickness are conducted at weekly intervals by a physician, with the severity of the lesion rated from 0 to 3. The final evaluation is usually carried out at the end of four to six weeks of treatment. Those lesions treated with $1\alpha,24\text{-}(OH)_2D_4$ have lower scores than the control lesions. An insignificant incidence of hypercalcemia is also observed.

EXAMPLE 22

Epidermal Cell Differentiation and Proliferation Testing

Human keratinocytes are cultured according to known modifications of the system originally described by Rheinwald and Green (*Cell*, vol. 6, p. 331(1975)). The $1\alpha,24$-dihydroxy vitamin $D_4$, dissolved in ethanol, is added to cells to yield a variety of concentrations between 0.05 and 5 µg/ml with the ethanol concentration not to exceed 0.5% v/v. Control cultures are supplemented with ethanol at a final concentration of 0.5% v/v.

Differentiation and proliferation of epidermal cells in culture is examined by:

1. quantitation of cornified envelopes;
2. quantitation of cell density of cells attached to disks;
3. monitoring transglutaminase activity; or
4. monitoring DNA synthesis by incorporation of $^3$H-thymidine.

Cultures incubated with $1\alpha,24$-dihydroxy vitamin $D_4$ have more cornified envelopes, fewer attached cells, higher transglutaminase activity, and lower DNA synthesis than control cultures.

EXAMPLE 23

Activity of $1\alpha,24\text{-}(OH)_2D_4$ in HL-60 Cell Differentiation Assay A dose-response study is conducted with $1\alpha,24\text{-}(OH)_2D_4$ in the HL-60 cell differentiation assay as described by DeLuca and Ostrom (DeLuca, H. F. and Ostrem, V. K., *Prog. Clin. Biol. Res.*, vol. 259, pp. 41–55 (1988)). In this study, $1\alpha,25\text{-}(OH)_2D_3$ is used as a positive control and appropriate solvents are used as negative controls. The following variables are evaluated: nonspecific acid esterase activity, nitroblue tetrazolium (NBT) reduction, and thymidine incorporation. The results show that $1\alpha,24\text{-}(OH)_2D_4$ has potent activity in promoting differentiation of HL-60 promyelocytes to monocytes.

EXAMPLE 24

Antiproliferative Activity of $1\alpha,24\text{-}(OH)_2D_4$ in Human Cancer Cell Lines Dose-response studies are conducted with $1\alpha,24\text{-}(OH)_2D_4$ in a battery of human cancer cell lines. These cell lines include, but are not limited to, the following: BCA-1 or ZR-75-1 (breast) and COL-1 (colon), as described by Shieh, H. L. et al. *Chem. Biol. Interact.*, vol. 81, pp. 35–55 (1982). In this study, appropriate solvents are used as negative controls. The results show that $1\alpha,24\text{-}(OH)_2D_4$ has potent (and reversible) antiproliferative activity, as judged by inhibition of thymidine incorporation.

EXAMPLE 25

Treatment of Psoriasis

An oral dosage formulation containing $1\alpha,24$-dihydroxyvitamin $D_4$ is evaluated in a double blind study for therapeutic efficacy of the formulation in the treatment of dermatitis (contact and ectopic). The formulation evaluated contains 1.0 to 10.0 µg of $1\alpha,24$-dihydroxyvitamin $D_4$. The control formulation is identical except that it does not contain the $1\alpha,24$-dihydroxyvitamin $D_4$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, background, etc.).

Evaluations of erythema, scaling, and thickness are conducted at weekly intervals by a physician. The final evaluation is usually carried out at the end of four to six weeks of treatment. The results of the study show that daily oral administration of 1,24-dihydroxyvitamin $D_4$ significantly reduces the degree of erythema, scaling, and thickness versus the control patients.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method of inhibiting hyperproliferative activity of human skin cancer cells, comprising treating the cancer cells with an effective amount of a compound of formula (I):

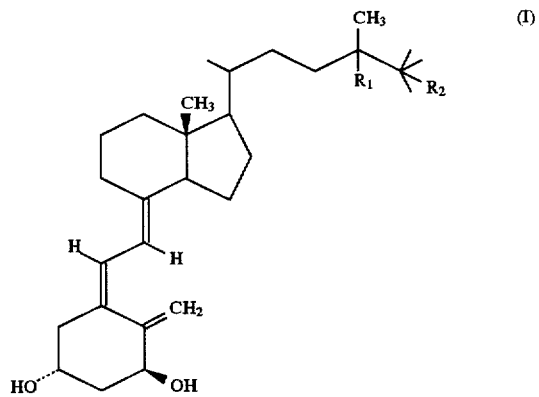

wherein $R_1$ is either H or OH and $R_2$ is either H or OH and salts, hydrates and solvates thereof.

2. The method of claim 1, wherein said amount is administered without causing hypercalcemia.

3. A method of treating psoriasis, comprising administering to a patient suffering from psoriasis a therapeutically effective amount of a compound of formula (I):

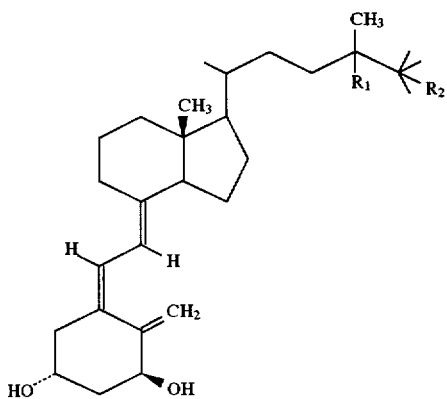

wherein $R_1$ is either H or OH and $R_2$ is either H or OH and salts, hydrates and solvates thereof.

4. The method of claim 3, wherein said amount is administered without causing hypercalcemia.

5. A method of treating a human to alleviate the cellular proliferative effects of human skin cancer, psoriasis, eczema, dermal hydration and sebum secretion, said method comprising administering to the human a therapeutically effective amount of a compound of formula (I):

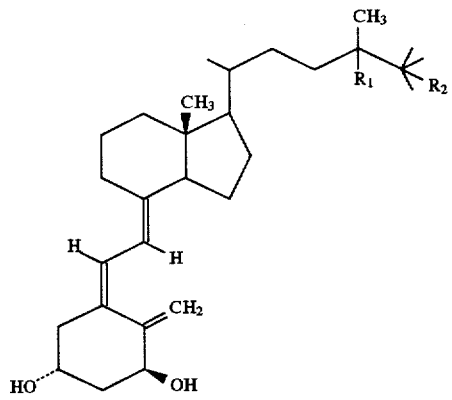

wherein $R_1$ is either H or OH and $R_2$ is either H or OH and salts, hydrates and solvates thereof.

6. The method of claim 5, wherein said amount is administered without causing hypercalcemia.

7. The method of any one of claims 1, or 3, or 5 wherein the compound of formula (I) is 1α,24-dihydroxy vitamin $D_4$.

8. The method of any one of claims 1, 3, or 5 wherein the compound of formula (I) is 1α,24(R)-dihydroxy vitamin $D_4$, substantially free of its (S) form.

9. The method of any one of claims 1, 3, or 5 wherein said amount is administered topically.

10. The method of claim 9, wherein said administering step further comprising administering a second agent selected from the group consisting of retinoids, chromanols, β-agonists, antiinflammatory agents, keratoplastic agents and combinations thereof.

11. The method of any one of claims 1, 3, or 5 wherein said amount is administered orally.

12. The method of any one of claims 1, 3, or 5 wherein said amount is administered parenterally.

13. A method of inhibiting hyperproliferative activity of human skin cancer cells, comprising treating the cancer cells with an effective amount of a compound of formula (I):

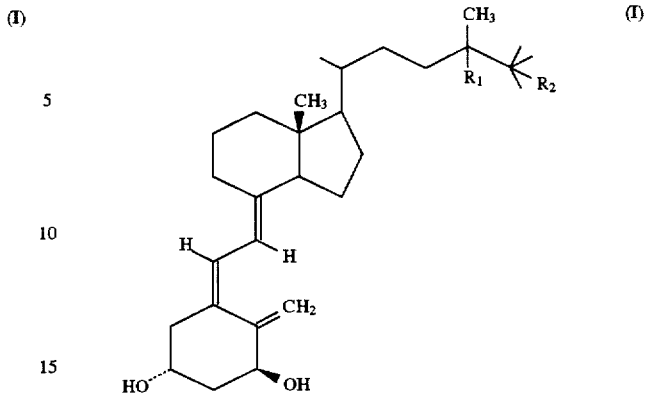

wherein $R_1$ is either H or OH and $R_2$ is either H or OH and salts, hydrates and solvates thereof, wherein said inhibiting of proliferative activity is measured by inhibition of thymidine uptake by said cancer cells.

14. A method of inhibiting hyperproliferative activity of human skin cancer cells, comprising treating the cancer cells with an effective amount of a compound of formula (I):

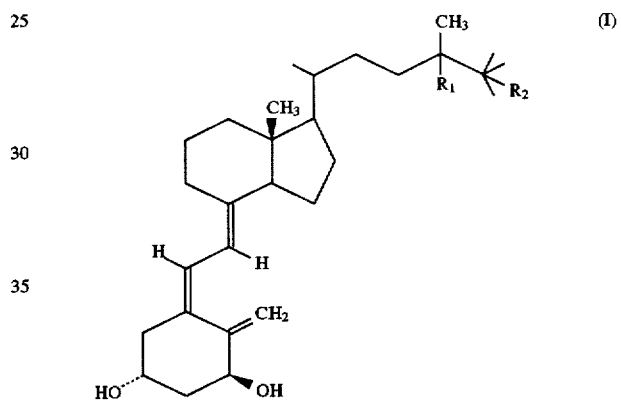

wherein $R_1$ is either H or OH and $R_2$ is either H or OH and salts, hydrates and solvates thereof, wherein said treating step comprises exposing skin cancer cells to an amount of 1α,24-dihydroxyvitamin $D_4$ sufficient to induce differentiation of said cancer cells to nonmalignant macrophages.

15. The method of claim 14 wherein said cells are human keratinocytes.

16. The method of any one of claims 13 or 14 wherein the compound of formula (I) is 1α,24-dihydroxy vitamin $D_4$.

17. The method of any one of claims 13 or 14 wherein the compound of formula (I) is 1α,24(R)-dihydroxy vitamin $D_4$, substantially free of its (S) form.

18. The method of any one of claims 13 or 14 wherein said amount is administered topically.

19. The method of claim 18, wherein said administering step further comprising administering a second agent selected from the group consisting of retinoids, chromanols, β-agonists, antiinflammatory agents, keratoplastic agents and combinations thereof.

20. The method of any one of claims 13 or 14 wherein said amount is administered orally.

21. The method of any one of claims 13 or 14 wherein said amount is administered parenterally.

* * * * *

UNITED STATES PATENT AND TRADEMARK OFFICE
CERTIFICATE OF CORRECTION

PATENT NO. : 5,763,428
DATED : June 9, 1998
INVENTOR(S) : KNUTSON, et al.

It is certified that error appears in the above-identified patent and that said Letters Patent is hereby corrected as shown below:

In Title, field [54], "1A-HYDROXY" should read --1α-HYDROXY--.

References Cited/OTHER PUBLICATIONS, second column, 2nd from last entry corresponding to "Chemical Abstracts, vol. 113, No.1,2 Jul.1990, ...(nisshin Flour Milling Co.).", "nisshin" should read --Nisshin--.

Col. 1, line 2, the Title, "1A-HYDROXY" should read --1α-HYDROXY--.

Col.1, line 7, "08/886,554" should read --07/886,554--.

Col. 4, line 30, "pseudohypoparathyhodism" should read --pseudohypoparathyroidism --.

Col. 12, line 27, "1a-vitamin $D_4$" should read --1α-vitamin $D_4$--.

UNITED STATES PATENT AND TRADEMARK OFFICE
CERTIFICATE OF CORRECTION

PATENT NO. : 5,763,428
DATED : June 9, 1998
INVENTOR(S) : KNUTSON, et al.

Page 2 of 2

It is certified that error appears in the above-identified patent and that said Letters Patent is hereby corrected as shown below:

In the printing of formula (I), in each of the following: Col. 3, lines 8-23, Col. 16, Claim 1, lines 44-9, Col. 17, Claim 3, lines 1-16, Col. 17, Claim 5 lines 26-42, Col. 18, Claim 13, lines 1-16, Col. 18, Claim 14, lines 25-40

"

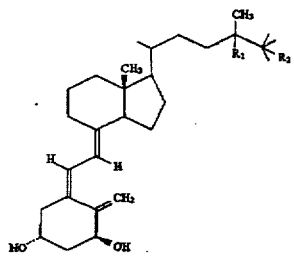

should read

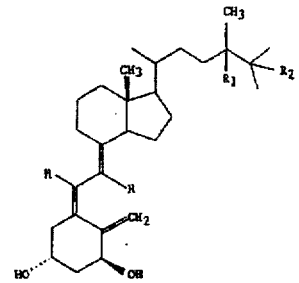

"

--.

Signed and Sealed this

Twenty-ninth Day of December, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,763,428
DATED : June 9, 1998
INVENTOR(S) : KNUTSON, et al.

It is certified that error appears in the above-identified patent and that said Letters Patent is hereby corrected as shown below:

On the title page, item item [56]:

In the References Cited/U.S. PATENT DOCUMENTS, first patent entry, "2,383,446 6/1945 Calcott et al.", the date of the reference "6/1945" should read --8/1945--.

In the References Cited/OTHER PUBLICATIONS, second column, 11th entry, "Martin and DeLuca, Am. J. Physiol. 216:1352-1359(1967)", the date of the reference "(1967)" should read --(1969)--.

Col. 2, line 66, "vitamin $D_2$" should read --vitamin $D_4$--.

Col. 3, line 5, "recepter" should read --receptor--.

Col. 3, line 27, " $R_1$=OH." should read --$R_1$=H and $R_2$=OH.--.

Col. 3, line 58, "5-methoxy" should read --6-methoxy--.

Col. 5, line 7, " administering administering" should read --administering--.

Col. 13, line 13, "regrain" should read --refrain--.

Col. 13, line 26, "contract" should read --contrast--.

Signed and Sealed this

Twenty-third Day of February, 1999

Q. TODD DICKINSON

*Attest:*

*Attesting Officer*  *Acting Commissioner of Patents and Trademarks*